(12) United States Patent
Wrue

(10) Patent No.: US 6,729,939 B2
(45) Date of Patent: May 4, 2004

(54) POLISHING METHOD FOR INTRAOCULAR LENS

(75) Inventor: Richard J. Wrue, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 10/022,101

(22) Filed: Dec. 17, 2001

(65) Prior Publication Data
US 2003/0114093 A1 Jun. 19, 2003

(51) Int. Cl.[7] .................................................. B24B 1/00
(52) U.S. Cl. .......................... 451/29; 451/442; 451/384
(58) Field of Search ................................ 451/442, 384, 451/390, 42, 32–35, 364, 29

(56) References Cited

U.S. PATENT DOCUMENTS

| | | | | |
|---|---|---|---|---|
| 2,380,653 A | * | 7/1945 | Kopplin | 451/33 |
| 4,580,371 A | * | 4/1986 | Akhavi | 451/32 |
| 4,856,234 A | | 8/1989 | Goins | 51/284 R |
| 5,133,159 A | | 7/1992 | Nelson | 51/313 |
| 5,571,558 A | | 11/1996 | Nguyen | 427/215 |
| 5,725,811 A | | 3/1998 | Nguyen | 264/2.7 |
| 5,769,889 A | | 6/1998 | Kelman | 623/6 |
| 5,961,370 A | * | 10/1999 | Valle et al. | 451/35 |
| 6,095,901 A | * | 8/2000 | Robinson et al. | 451/35 |

FOREIGN PATENT DOCUMENTS

| | | | |
|---|---|---|---|
| EP | 0 215 261 A2 | 3/1987 | |
| WO | 02/08131 A1 | 1/2002 | C03B/33/08 |
| WO | 02/16077 A2 | 2/2002 | B24B/31/10 |

OTHER PUBLICATIONS

USSN 10/184,167 Entitled "Apparatus and Method for Target Polishing Intraocular Lenses", filed Jun. 27, 2002 by G. Green.

USSN 10/184,552 Entitled "Method for Polishing Intraocular Lenses", filed Jun. 27, 2002 by G. Green.

*Posterior Capsule Opacification* by Nishi, *Journal of Cataract & Refractive Surgery*, vol. 25, Jan. 1999.

* cited by examiner

*Primary Examiner*—Robert A. Rose
(74) *Attorney, Agent, or Firm*—Katherine McGuire

(57) ABSTRACT

A method for removable attachment of a mask to an IOL to protect a sharp peripheral edge of the IOL optic during polishing.

2 Claims, 2 Drawing Sheets

POLISHING METHOD FOR INTRAOCULAR LENS

BACKGROUND OF THE INVENTION

The present invention relates to the manufacture of intraocular lenses (IOLs) for implantation in an eye. The present invention more particularly relates to a method of providing a protective mask for removable attachment to selected areas of an IOL during polishing of the IOL.

IOLs require highly polished surfaces free of surface irregularities. This is because the IOL is in direct contact with delicate eye tissues and any rough or non-smooth surface on an IOL may cause irritation or abrading of tissue or other similar trauma to the eye. It has been found that even small irregularities can cause irritation to delicate eye tissues.

IOLs are typically either molded or lathe cut. Subsequent to either of these operations, the IOLs usually have irregular or roughened surfaces that need to be smoothed. It is thus usually necessary to polish the IOL to smooth out any rough areas on the IOL. One known polishing method is tumble polishing wherein a batch of IOLs are placed in a tumbler for several hours with a polishing agent. Examples of tumble polishing IOLs may be seen in the following patents:

U.S. Pat. No. 5,133,159 discloses a method of tumble polishing silicone articles in a receptacle charged with a mixture of non-abrasive polishing beads and a solvent which is agitated to remove surface irregularities from the articles.

U.S. Pat. No. 5,571,558 discloses a tumbling process for removing flash from a molded IOL by applying a layer of aluminum oxide on a plurality of beads, placing the coated beads, alcohol, water and silicone IOLs in a container and tumbling the same to remove flash.

U.S. Pat. No. 5,725,811 discloses a process for removing flash from molded IOLs including tumbling the IOLs in a tumbling media of 0.5 mm diameter glass beads and 1.0 mm diameter glass beads, alcohol and water.

In recent years, IOLs have been purposely designed with sharp posterior edges which has been found to inhibit the unwanted growth of lens epithelial cells (LECs) between the IOL and posterior capsular bag, also known as posterior capsule opacification or "PCO" to those skilled in the art. One such method for creating a sharp posterior edge in an IOL is described in copending application Ser. No. 10/403,989 filed on Mar. 31, 2003 and of common ownership with the present application, the entire disclosure of which is incorporated herein by reference. Creating a sharp, discontinuous bend in the posterior capsule wall is widely recognized by those skilled in the art as an effective method for minimizing PCO. See, for example, *Posterior Capsule Opacification* by Nishi, *Journal of Cataract & Refractive Surgery*, Vol. 25, January 1999. This discontinuous bend in the posterior capsule wall can be created using an IOL having a posterior edge which forms a sharp edge with the peripheral wall of the IOL.

Thus, while polishing is a necessary step in the IOL manufacturing process to remove surface irregularities, a purposely formed, sharp, posterior edge is one area of the IOL which should not be polished. If this area of the IOL is not masked from the polishing operation, the sharp posterior edge will become rounded and not function to inhibit PCO as intended. There thus remains a need for a method for polishing IOLs having sharp posterior edges wherein selected areas of the IOL, namely the sharp posterior edge, is protected from the rounding effect of the polishing operation.

SUMMARY OF THE INVENTION

The present invention addresses the problem of protecting the sharp posterior edge of an IOL during the polishing operation by providing a removable mask for attaching to a respective IOL prior to subjecting the IOL to polishing. The mask is configured to cover only the sharp peripheral edge of the IOL such that only this selected area of the IOL is not polished during the polishing operation. In a preferred embodiment, the mask is made of an elastomeric material which can stretch to alternately insert and remove an IOL therefrom in a manner which will not harm the delicate IOL. The elastomeric material absorbs the force of the polishing action and thus protects the sharp posterior edge from becoming rounded during the polishing operation.

DETAILED DESCRIPTION

As stated in the Background section hereof, an undesirable post-surgical condition of intraocular lens implant surgery known as posterior capsule opacification or PCO may occur which happens when an implanted IOL becomes clouded and is no longer able to properly direct and focus light therethrough. The main cause for this condition is the mitosis and migration of lens epithelial cells (LECs) across the posterior surface of the lens capsule behind the IOL optic. In an eye where the natural crystalline lens has been damaged (e.g., clouded by cataracts), the natural lens is no longer able to properly focus and direct incoming light to the retina and images become blurred. A well known surgical technique to remedy this situation involves removal of the damaged crystalline lens which may be replaced with an artificial lens known as an intraocular lens or IOL such as prior art IOL 24 seen in FIG. 1. Although there are many different IOL designs as well as many different options as to exact placement of an IOL within an eye, the present invention concerns itself with an IOL having a sharp posterior edge for implanting inside the capsule of an eye (not shown). This implantation technique is commonly referred to in the art as the "in-the-bag" technique. In this surgical technique, a part of the anterior portion of the capsular bag is cut away (termed a "capsularhexis") while leaving the posterior capsule intact.

Figure 1:
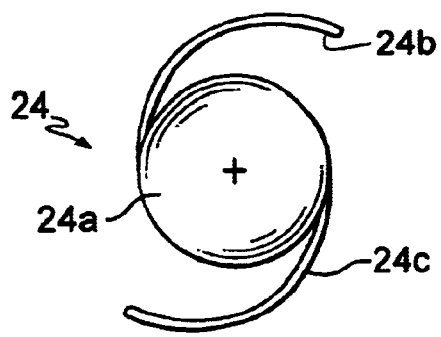
FIG. 1 is a plan view of a common IOL design.

Thus, in the "in-the-bag" technique of IOL surgery, the IOL is placed inside the capsule which is located behind the iris in the posterior chamber of the eye. As seen in FIG. 1, an IOL includes a central optic portion 24a which simulates the extracted natural lens by directing and focusing light upon the retina, and further includes means for securing the optic in proper position within the capsular bag. A common IOL structure for anchoring the IOL in the eye is called a haptic which is a resilient structure extending radially outwardly from the periphery of the optic. In a particularly common IOL design, two haptics 24b, 24c extend from opposite sides of the optic and curve to provide a biasing force against the inside of the capsule which secures the IOL in the proper position within the capsule.

The posterior surface of the capsule touches the posterior surface of the IOL optic 24a. When the damaged natural lens is surgically removed, a number of LECs may remain within the capsule, particularly at the equator thereof which is the principle source of germinal LECs. Although a surgeon may attempt to remove all LECs from the capsular bag at the time of IOL implantation surgery, it is nearly impossible to remove every single LEC. Any remaining LECs can multiply and migrate along the posterior capsule wall 16. This is especially true in IOLs having rounded edges, where it has been found that clinically significant PCO results in about 20%–50% of patients three years post surgery. A presently popular and effective method of preventing PCO is to create a sharp, discontinuous bend in the posterior capsule wall as explained in the Background section hereof.

Figure 2:
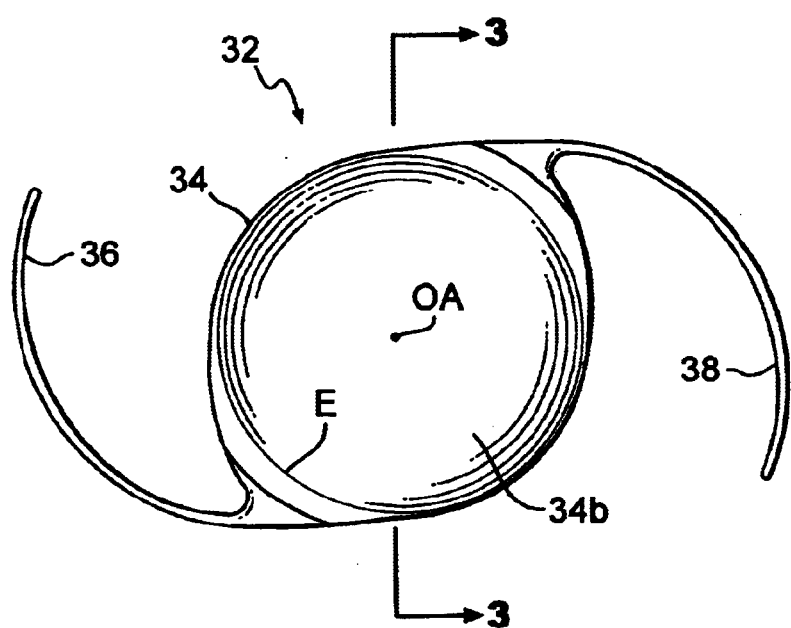
FIG. 2 is a plan view of an IOL having a sharp posterior edge design.
Figure 3:
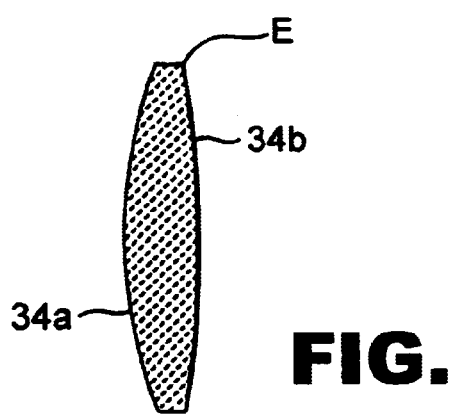
FIG. 3 is a cross-sectional view of the IOL as taken generally along the line 3—3 of FIG. 2.

Referring now to FIGS. 2 and 3, an IOL 32 is shown which includes a central optic portion 34 having opposite anterior and posterior surfaces 34a and 34b, respectively. When implanted within the eye, anterior optic surface 34a faces the cornea and posterior optic surface 34b faces the retina. A pair of haptics 36,38 are attached to and extend from opposite sides of the periphery of optic portion 34 and are configured to provide a biasing force against the interior of the capsule to properly position IOL 32 therein. More particularly, the haptics 36,38 are configured such that upon implanting the IOL with the capsular bag, the haptics engage the interior surface of the capsular bag. The engagement between the haptics and capsule creates a biasing force causing the IOL optic 34 to vault posteriorly toward the retina whereupon the posterior surface 34b of the IOL optic presses tightly against the interior of the posterior capsule wall of the capsule. It is noted that other known IOL positioning means are possible and within the scope of the invention. Furthermore, IOL 32 may be made from any suitable IOL material, e.g., PMMA, silicone, hydrogels and composites thereof. The IOL 32 may also be a one piece or multiple piece design (e.g. where the haptics are attached to the optic after the optic is formed.)

Referring still to FIGS. 2 and 3, it is seen that IOL optic 34 has a periphery including a sharp edge E defined at the juncture of posterior surface 34b and peripheral wall P. With the haptics 36,38 providing the biasing force explained above, the optic posterior surface 34b presses tightly against the posterior capsule wall. Since the lens capsule is somewhat resilient in nature, the force of the IOL optic against the capsule wall results in the IOL indenting into the posterior capsule wall. The sharp edge E of the IOL optic thus forcibly indents into the capsule wall and thereby creates a discontinuous bend in the posterior capsule wall at this point. As explained above, this discontinuous bend in the posterior capsule wall acts to inhibit LEC migration past this point (i.e., between the posterior capsule wall and IOL posterior surface 34b) and PCO is substantially inhibited.

Figure 4:
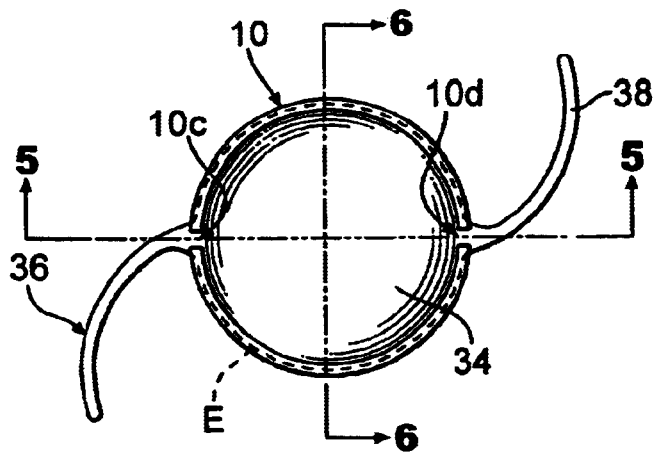
FIG. 4 is a plan view of an IOL having a sharp posterior edge inserted into the mask of the present invention.
Figure 5:
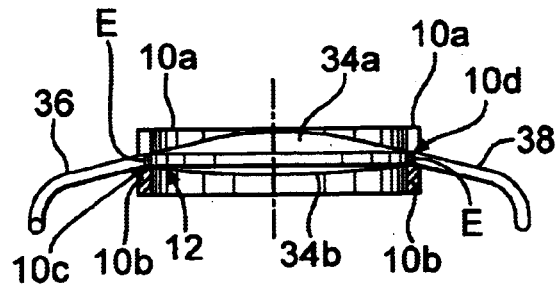
FIG. 5 is a cross-sectional view as taken generally along the line 5—5 of FIG. 4.
Figure 6:
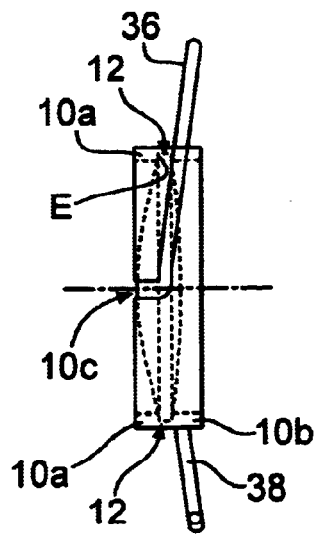
FIG. 6 is a side elevational view thereof.

Referring now to FIGS. 4–6, discussion is turned to the inventive mask designated by reference numeral 10 which may be alternately attached and removed from an IOL having a sharp posterior edge, such as IOL 34, to cover and protect the sharp posterior edge E thereof during the polishing of IOL 34. Once polishing is completed, mask 10 is removed from IOL 34 to reveal the still sharp posterior edge E thereof. The IOL 34 may then processed further as desired (e.g., hydration, sterilization and packaging).

Mask 10 is preferably made of an elastomeric material which is sufficiently resilient to permit attachment to and removal from an IOL in the manner explained below. Mask 10 is configured as a unitary piece which is shaped and sized to approximate the corresponding shape and size of the periphery of the respective IOL optic 34a. An interior annular groove 12 is formed and defined in mask 10 by anterior and posterior mask segments 10a and 10b and wherein the sharp peripheral edge E of IOL 34 is removably inserted and thereby masked. Since mask 10 is resilient, insertion of an IOL therein requires a radial stretching of mask 10 allowing insertion of the IOL periphery therein. Once in place, the stretching force on mask 10 is released allowing mask 10 to relax and conform to the IOL periphery. Since it is not necessary to mask the haptics 36,38, a pair of diametrically opposed through holes 10c and 10d are provided in mask 10 wherethrough haptics 36,38 may be respectively inserted at the time of inserting IOL in mask 10, with haptics 36,38 freely extending therefrom.

Once attached to a respective IOL in this manner, the sharp peripheral edge E of IOL 34 is protected by mask 10 inside groove 12 while the remainder of the IOL is left exposed. As such, the polishing of IOL will affect only the exposed areas of the IOL, leaving the sharp peripheral edge E of the IOL unpolished and sharp, as intended. Once polishing is complete, mask 10 is removed by again stretching it radially whereupon clearance is provided to remove the IOL therefrom while withdrawing haptics 36,38 back through holes 10c, 10d, respectively. Being of relatively simple design and materials, mask 10 may be made cheaply by injection molding, for example, such that it can be discarded after a single use.

What is claimed is:

1. A method of polishing an intraocular lens having an optic having a sharp peripheral edge and one or more haptics extending from the optic, said method comprising the steps of:

a) providing an elastomeric mask having an internal annular groove and a throughhole for each of said haptics;

b) positioning said optic sharp peripheral edge in said internal annular groove with each said haptic extending through a respective said throughhole;

c) subjecting said intraocular lens to a polishing operation whereby said sharp peripheral edge is protected by said mask; and d) removing said intraocular lens from said mask.

2. The method of claim 1 wherein during said positioning and removing steps, said mask is stretched to alternately position and remove an intraocular lens therefrom.

* * * * *